(12) United States Patent
Koch

(10) Patent No.: US 8,076,640 B2
(45) Date of Patent: Dec. 13, 2011

(54) METHOD AND DEVICE FOR MEASURING ELECTRON DIFFRACTION OF A SAMPLE

(75) Inventor: Christoph T Koch, Goeppingen (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 322 days.

(21) Appl. No.: 12/549,029

(22) Filed: Aug. 27, 2009

(65) Prior Publication Data

US 2011/0049363 A1   Mar. 3, 2011

(51) Int. Cl.
 *G01N 23/20*   (2006.01)
(52) U.S. Cl. .................. 250/307; 250/310; 250/311
(58) Field of Classification Search ............ 250/307
 See application file for complete search history.

(56) References Cited

U.S. PATENT DOCUMENTS 5,552,602 A * 9/1996 Kakibayashi et al. ........ 250/311
 6,548,811 B1 * 4/2003 Nakamura et al. ............ 250/311
 7,154,091 B2 * 12/2006 Zewail et al. ................. 250/311

OTHER PUBLICATIONS

Eades, "Zone-axis patterns formed by a new double-rocking technique", Ultramicroscopy 5, pp. 71-74 (1980).
Gatan Inc., http://www.gatan.com/imaging/dig_micrograph.php (2009).
Koch, "Many-Beam Solution to the Phase Problem in Crystallography" (arXiv:0810.3811v1 [cond-mat.mtrl-sci], http://arxiv.org/abs/0810.3811v1) publication date: Oct. 21, 2008.
Koch, Presentation documents: StEM "Large Angle Rocking Beam Electron Diffraction" presented in public at "European Microscopy Congress" in Aachen, Germany, presentation date: Sep. 1, 2008.
Koch et al., "A useful expansion of the exponential of the sum of two non-commuting matrices, one of which is diagonal", J. Phys. A: Math. Gen. 36, pp. 803-816 (2003).
Koch et al., "Software Precession Electron Diffraction" 14th European Microscopy Congress EMC 2008, Sep. 1-5, 2008, Aachen, Germany M. Luysberg, K. Tillmann, T. Weirich (Eds.):, vol. I: Instrumentation and Methods, pp. 201-202, DOI: 10.1007/978-3-540-85156-1_101, Springer-Verlag Berlin Heidelberg 2008, publication date: Aug. 29, 2008.
Koch et al., Presentation documents published on Internet at mhtml:http://www.mf.mpg.de/INCEMS/Koch08_SPED_online.mhtlKoch08_SPED_online-Dateien/frame.htm, pp. 1-18, saved as "10_presentation_p1" to "10_presentation_p18", publication date: Sep. 8, 2008.
Nanomegas, http://web.archive.org/web/20071025004948/http://www.nanomegas.com/index.php (Oct. 2007).

(Continued)

*Primary Examiner* — Phillip A Johnston
(74) *Attorney, Agent, or Firm* — Caesar, Rivise, Bernstein, Cohen & Pokotilow, Ltd.

(57) ABSTRACT

The invention relates to a method and a device for measuring electron diffraction of a sample, including the steps of illuminating the sample with an incident electron beam which is deflected from a sample axis to hit the sample at an angle of incidence relative to the sample axis, at least partially subjecting the incident electron beam to diffraction by the sample, subjecting the diffracted and undiffracted electron beams transmitted through the sample to a partial deflection compensation, detecting the intensity of the diffracted and undiffracted electron beams transmitted through the sample in dependency on the angle of incidence and a scattering angle of the diffracted beam. The invention also relates to a computer program for controlling a transmission electron microscope for carrying out the inventive method.

25 Claims, 2 Drawing Sheets

OTHER PUBLICATIONS

Treacy et al., "Variable Coherence Microscopy: a Rich Source of Structural Information from Disordered Materials", Acta Cryst. A52, p. 212 (1996).

Vincent et al., "Double conical beam-rocking system for measurement of integrated electron diffraction intensities", Ultramicroscopy 53, pp. 271-282 (1994).

* cited by examiner

A)    B) PRIOR ART

METHOD AND DEVICE FOR MEASURING ELECTRON DIFFRACTION OF A SAMPLE

BACKGROUND

1. Field of Invention

The invention relates to a method for measuring electron diffraction of a sample by transmission. The invention further relates to a device for deflecting an electron beam incident on a sample and diffracted and undiffracted electron beams transmitted through the sample.

Electron diffraction is a well known method in the field of crystallography for obtaining structure information about crystals. In electron diffraction methods an electron beam is directed onto a sample diffracted by the atomic structure of the sample. Depending on the structure of the sample, like a crystal lattice structure, diffraction leads to reflections at distinct scattering angles, including Bragg reflections. The intensities of the diffracted reflections can be detected as a function of the scattering angle. Such measurement of diffracted intensities as a function of the scattering angle will be called a diffraction pattern within this application. From the measured intensities in the diffraction pattern information about the structure of the samples can be obtained. Electron diffraction can be measured by transmission or by reflection.

2. Description of Related Art

Due to a strong interaction between the scattered electrons and the sample material electron diffraction for crystallography is especially useful for determining the atomic structure of small crystalline volumes. The strong interaction of electrons with the sample material in electron diffraction measurements causes the electrons to scatter multiple times within the sample. This dynamical scattering leads to difficulties in the analysis of measured intensity data for structure determination. Also, by detecting the intensities of the diffracted beams, information about the phase of the diffracted electron beams is lost. This phase information is important for reconstructing the sample structure from the diffraction pattern. Therefore, for obtaining structure information from an intensity diffraction pattern, phase information must be reconstructed during the data analysis. Structure determination from x-ray-scattering methods usually makes use of the kinematic approach for solving the phase problem and analyzing measured intensity data. The kinematic theory neglects dynamical effects due to multiple scattering in the sample and is widely applicable for x-ray scattering methods. In electron scattering methods, because of the multiple scattering, the kinematic theory is not generally directly applicable. For reducing dynamical scattering effects due to multiple scattering, very thin samples are usually preferred.

Other methods for reducing the dynamic effects on electron diffraction patterns and thus enabling the application of the kinematic theory for data analysis include, for example, precession electron diffraction (PED).

In this approach described by R. Vincent and P. A. Midgley "Double conical beam-rocking system for measurement of integrated electron diffraction intensities" Ultramicroscopy 53 (1994) 271-282, an electron beam illuminating a sample is conically scanned around the optical axis. Below the sample, the transmitted and diffracted beam is de-scanned for compensating the deflection of the incident beam from the optical axis. As a consequence, diffracted intensities integrated over the various angles of incidence which the incident electron beam assumes during scanning, are detected in the diffraction pattern. In the method described by Vincent and Midgley, a complete de-scanning of the beam below the specimen is essential for an efficient reduction of dynamical effects and measurement of the integrated Bragg intensities relative to a diffuse scattering background. Integrating the measured intensities over the various angles of incidence, however, leads to a loss of structural information.

On the other hand, it is known that disc-shaped diffraction patterns of distinct reflections produced from convergent beam electron diffraction (CBED) can be used for solving the phase problem even if the electrons have scattered multiple times (C. T. Koch and J. C. H. Spence in J. Phys. A: Math. Gen. 36 (2003) 803-816 "A useful expansion of the exponential of the sum of two non-commuting matrices, one of which is diagonal"). In CBED methods the sample is illuminated by a convergent beam having a specific convergence angle. The convergent beam therefore includes beam fractions hitting the sample under various angles of incidence up to the convergence angle. The various angles of incidence included in the convergent incident beam lead to a shift of the diffraction pattern for each angle of incidence. Thus each reflection in the CBED diffraction pattern has the shape of a disk. The larger the convergence angle, the larger the diameter of the reflections in the diffraction pattern. Therefore, the angular range, which can be reached with convergent beam electron diffraction is limited by half the distance between adjacent Bragg peaks in the diffraction pattern. If the angular range exceeds this limit, adjacent reflections overlap in the diffraction pattern and cannot be resolved any more. Therefore, the structural information which can be obtained with this method is limited.

All references cited herein are incorporated herein by reference in their entireties.

SUMMARY OF THE INVENTION

In view of above mentioned problems, it is therefore an objective of the invention, to provide an improved method and device for electron diffraction measurements which at least partially overcomes above mentioned problems.

The objective is achieved by the method and device of the invention.

The inventive method for measuring electron diffraction of a sample comprises the steps of illuminating the sample with an incident electron beam which is deflected from a sample axis to hit the sample at an angle of incidence relative to the sample axis, at least partially subjecting the incident electron beam to diffraction by the sample, subjecting the diffracted and undiffracted electron beams transmitted through the sample to a partial deflection compensation, and detecting the intensity of the diffracted and undiffracted electron beams transmitted through the sample in dependency on the angle of incidence and a scattering angle of the diffracted beams.

According to a further aspect of the invention, a device is provided configured for deflecting electron beams in a transmission electron diffraction setup, comprising a beam deflection device, configured for deflecting an electron beam illuminating a sample such that the beam hits the sample at an angle of incidence with respect to a sample axis, and an exit beam deflection compensation device, configured for subjecting a beam transmitted through the sample to partial deflection compensation.

According to a still further aspect of the invention a device configured for deflecting electron beams of a transmission electron microscope (TEM) is provided, comprising a beam deflection device, configured for operating a transmission electron microscope such that an electron beam illuminating a sample is deflected to hit the sample at an angle of incidence with respect to a sample axis, and an exit beam deflection compensation device, configured for operating a transmission electron microscope such that an electron beam transmitted through the sample is subjected to partial deflection compensation. The objective of the invention is further solved with a transmission electron microscope comprising a device for deflecting electron beams.

The objective is further achieved by a computer program product or a digital storage medium with electronically readable data, containing a program code for controlling a transmission electron microscope for carrying out the inventive method.

BRIEF DESCRIPTION OF THE DRAWINGS

Further aspects of the invention will become apparent from the description relating to the accompanying drawings which schematically show in FIG. 1: the measuring geometry of the inventive method.

DETAILED DESCRIPTION OF PREFERRED EMBODIMENTS

Figure 3:
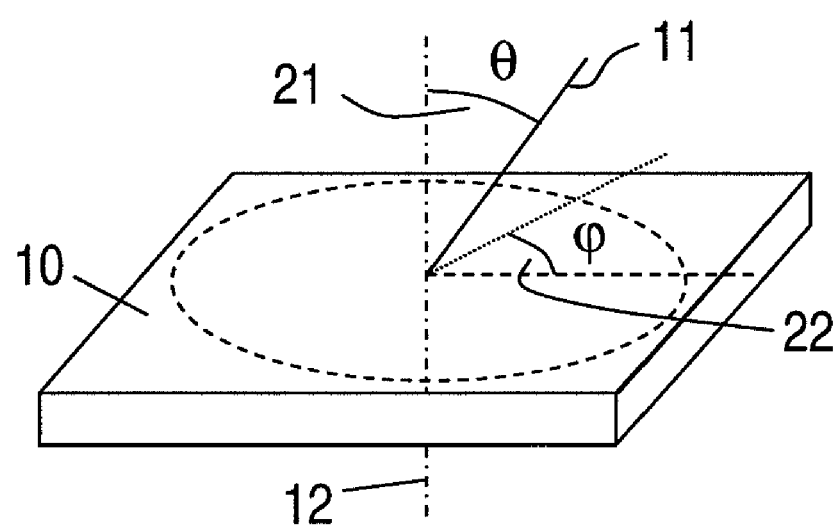
FIG. 3: an illustration of the angle of incidence with respect to the sample axis.

According to the inventive method, the incident electron beam hits a sample at an angle of incidence relative to a sample axis. The sample axis is an axis having a fixed orientation with respect to the sample. The sample axis can for example be a surface normal to a slide-shaped sample. Preferably, the sample axis is collinear with an optical axis of the experimental setup, e.g., a transmission electron microscope. The angle of incidence with respect to the sample axis comprises two components, the inclination angle $\theta$ and the azimuth angle $\phi$ as illustrated in FIG. 3. The inclination angle $\theta$ is preferably larger than 0.

A part of the electron beam illuminating the sample is transmitted through the sample undiffracted and at least part of the electron beam is diffracted by the atomic structure of the sample. Accordingly, the electron beam transmitted through the sample comprises undiffracted and diffracted beams which emanate from the sample under various scattering angles. This leads to reflections at particular scattering angles in the diffraction pattern. The different reflections are typical for the lattice structure of the sample and can be indexed as known in the art of crystallography. The sample preferably comprises a material sensitive to electron diffraction and can comprise, for example: a two-dimensional crystal, a three-dimensional crystal, a protein crystal, a quasicrystal or even a single grain selected by the electron beam from a polycrystalline material.

Within a reference frame fixed on the sample, when the incident beam hits the sample at an angle of incidence with respect to the sample axis at an inclination angle larger than 0, the scattering angles of the diffraction reflections are also deflected leading to a shift of the reflections in the diffraction pattern relative to the diffraction pattern obtained by the incident beam being parallel to the sample axis. According to the invention, the diffracted and undiffracted electron beams transmitted through the sample are subjected to a partial deflection compensation. By this measure the shift of the reflections in the diffraction pattern can be reduced. The position of the different diffraction reflections of an undeflected incident beam, i.e. the position of the diffraction reflections if the inclination angle of incidence is 0, is determined by the lattice structure of the sample (and the energy of the electron beam) and remains fixed on the diffraction pattern. This position will be referred to as actual reflection position within this application. The diffraction reflection produced by the deflected beam however is shifted in the diffraction pattern. This shift is reduced by the partial deflection compensation of the diffracted beam. Consequently, the distance between the diffraction reflection and the actual reflection position is reduced.

Partial deflection compensation may also include any kind of deflection of the diffracted intensities which still allows the diffraction reflections to be mapped to a specific diffraction spot and deflection angle of the incident electron beam. Partial deflection compensation therefore includes a deflection of the transmitted and diffracted beams in which, for example, the distance between the deflected diffraction reflection and the actual reflection position is reduced but the deflected diffraction reflection is rotated around the actual reflection position. A special case of this example is deflection overcompensation in which case this rotation is 180°. Partial deflection compensation shall be understood as leading to a reduction of the distance between the deflected diffraction reflection and the actual reflection position, irrespective of their relative orientation.

The intensities of the transmitted undiffracted and diffracted beams are detected in dependency on the angle of incidence and the scattering angles. Since the incident beam deflection is not fully compensated in the diffracted beams, information about the angle of incidence and the scattering angle is included in the detected diffraction pattern. On the other hand due to the partial deflection compensation, an overlap of different diffraction reflections in the diffraction pattern can be avoided even if a large range of angles of incidence is included. The detected intensity in the diffraction pattern can be unambiguously attributed to individual diffraction reflections and deflection angles of the incident electron beam. Thus, the information included in a diffraction pattern detected as the diffracted and undiffracted intensity in dependency on the angle of incidence and the scattering angle can be increased with respect to conventional methods.

Preferably, the sample axis is collinear with an optical axis of the experiment and remains fixed. In this case, deflection of the incident electron beam from the sample axis is achieved with a beam deflection device, preferably comprising electron optics components. Such electron optics components can for example be deflection coils driven by an electric current flowing through the coils as commonly used for aligning the electron beam in electron diffraction experiments. Alternatively, the incident electron beam can be aligned with the optical axis and the deflection of the incident beam from the sample axis is achieved by changing the orientation of the sample relative to the optical axis and deflecting the diffracted and undiffracted beams by the same azimuth as the sample axis, but with a smaller tilt angle. This can be achieved by a computer controlled sample stage suitable for tilting the sample in different directions. It is however preferred that the sample remains fixed with the sample axis aligned with the optical axis and the angle of incidence is chosen by beam deflection.

According to a preferred embodiment, the inventive method further comprises the step of varying the angle of incidence under which the electron beam hits the sample by deflecting the electron beam with a beam deflection device. In this case the change in angle of incidence of the electron beam may be obtained by either tilting a sample stage with drives for changing the orientation tilt of the sample in order to produce a rocking movement of the sample, or, preferably, by deflecting the incident electron beam using a beam deflection device comprising electron optics components such as deflection coils for deflecting the electron beam from the optical axis or sample axis. In both cases the inclination of the incident beam relative to the sample axis must be partially compensated by deflecting the transmitted diffracted and undiffracted beams as described above. The step of varying the angle of incidence, at which the electron beam hits the sample leads to the advantage that the reflections can be detected under various angles of incidence in one diffraction pattern data set. The partial deflection compensation allows an inclination of the incident beam much larger than half the Bragg angle to be used without an overlap of different reflections. From such diffraction pattern containing a number of various reflections at various angles of incidence an increased structure information and phase information can be obtained.

The intensity of the transmitted and diffracted electron beams is preferably detected two-dimensionally as a function of the angle of incidence and the scattering angle. The intensity can be detected for example with two-dimensional position sensitive detectors such as for example CCD detectors, image plates, or electron sensitive photographic film. Further, the scattered intensities can be detected two-dimensionally by scanning with a one-dimensional position sensitive detector or even scanned with a point detector. A detection of the diffraction pattern with a two-dimensional detector device leads to the advantage, that several reflections can be detected at the same time for each angle of incidence. When the angle of incidence is varied, the detected intensity for the various scattering angles can be accumulated in one data file, or a separate data file can be obtained for each angle of incidence.

According to the invention, the diffraction shift is partially compensated, in order to avoid an overlap of different reflections. In principle, the compensation of the deflection can be achieved electronically by data analysis after detection for example by a point detector. Preferably, however, the partial deflection compensation according to the invention is achieved by way of an exit beam deflection device prior to detection. This leads to the advantage that even large angle reflections can be shifted onto a two-dimensional detector, which could otherwise eventually be outside the surface of the detector and thus of the detectable range.

The exit beam deflection device preferably comprises electron optics components, such as for example deflection coils. As generally known in the art, couples of deflection coils can be arranged around an electron beam. Depending on an electric current flowing through the coils, the direction of the electron beam can be deflected. Consequently, by controlling the value of an electric current flowing through the deflection coils, the direction of an electron beam can be controlled. Such deflection coils are usually comprised in conventional transmission electron microscopes.

In the inventive method, the incident electron beam is preferably a substantially parallel beam. A substantially parallel beam shall be understood to be an electron beam having only a small convergence angle of, for example, typically 1 mrad or less for an electron beam of 200 keV. Depending on the dimensions of the crystal lattice structures such as the unit cell of the sample material, however, a convergence angle as large as for example 5 mrad, may also be possible. A smaller convergence angle allows for a better resolution of the angle of incidence and scattering angle of the detected diffraction pattern.

The electron beam preferably has an energy in the range between 20 keV and 3000 keV and a preferred band width of less than ±1 eV. An energy range of the electron beam of 20 keV to 300 keV is even more preferred. The electron beam can also be a monochromated beam (e.g., energy width of less than 0.5 eV), but does not necessarily have to.

In a preferred variant of the inventive method, the angle of incidence of the incident electron beam is varied by scanning the angle of incidence over an angular range around the sample axis. Preferably, in this mode, all scanned angles have the same absolute inclination angle $\theta$, but differing azimuth angles $\phi$. In another preferred variant, the angle of incidence is scanned over a two-dimensional range around the sample axis with a maximum inclination angle $\theta_{MAX}$, wherein the two-dimensional range can be, for example, a circular range, an elliptical range, or a square range. In this mode, not only the azimuth angle $\phi$ is varied but also the inclination angle $\theta$. Other two-dimensional shapes of the scanning range are also possible in principle.

By scanning the angle of incidence over the two-dimensional circular range, illumination of a sample with a convergent beam is simulated with the difference that with the inventive method, each angle of incidence is measured separately one by one, while with a convergent beam, all angles of incidence up to the convergence angle, which corresponds to the maximum inclination angle $\theta_{MAX}$, are measured at the same time. In conventional convergent beam electron diffraction (CBED) methods illumination of the sample with a convergent beam leads to disc-shaped reflections in the diffraction pattern, as measured for example with a two-dimensional detector. With the inventive method, the deflection angle for each angle of incidence is partially compensated after diffraction from the sample, so that the radius of the disc-shaped diffraction pattern of each reflection is reduced. The actual reflection positions however remain fixed and are represented by the center points of the disc-shaped reflections in the diffraction pattern.

This leads to the advantage that even large angles of incidence, e.g., up to 100 mrad, can be chosen for illuminating the sample, while at the same time an overlap of adjacent diffraction reflections can be avoided. The disc or annular shaped reflection patterns of each particular reflection in the diffraction pattern includes the information about the angle of incidence and the scattering angle of the diffracted intensities. The possibility to cover a very large range of directions of the incident electron beam without producing an overlap of adjacent diffraction reflections leads to additional structure information in the measured diffraction pattern which can not be obtained with conventional scattering methods including convergent beam electron diffraction and the above mentioned double conical beam rocking system with complete deflection compensation.

Scanning the angle of incidence over an annular range around the sample axis leads to annular shaped diffraction patterns of each diffraction reflection. By partial compensation of the deflection angle, the size and diameter of the ring shaped diffraction reflections are reduced and may thus be prevented from overlapping even for large inclination of the incident beam.

While the variant of scanning the angle of incidence over a two-dimensional range around the sample axis is suitable for obtaining more information, because more different angles of incidence are covered within this mode, scanning the angle of incidence over an annular range around the sample axis leads to the advantage that the time necessary for such measurements is reduced, because the number of angles of incidence, to which the incident beam has to be aligned can be reduced.

Preferably, a degree of partial deflection compensation can be chosen in dependency on a maximum angle of incidence of the incident beam and the distance of the actual reflection positions in the diffraction pattern. The degree of partial deflection compensation relates to the ratio of the reduction of the distance of the diffraction reflection from the actual reflection position. The degree of partial deflection compensation can be chosen, for example, in the range from 99% close to full compensation and 1% compensation. Preferably, the degree of compensation can be chosen in a range from 5% or 10% up to 90% or 95%. A complete compensation of one hundred percent would lead to a complete loss of the structure information in the disc-shaped or annular-shaped diffraction reflections. A further parameter for limiting the degree of compensation is the spatial resolution of a two-dimensional detector. Structural information in the disc-shaped reflection can also be lost, if the reflections are compressed by too high a partial compensation and consequently can be detected only by a small number of detector pixels. With zero compensation, i.e. without compensation, as already explained above, adjacent reflections would overlap in the diffraction patterns, in case of large angles of incidence. Therefore the degree of compensation is preferably chosen, such that the diffraction patterns of adjacent reflections in the diffracted beams do not overlap even with a maximum deflection angle of incidence of the incident beam.

In a preferred embodiment of the inventive method, the method further comprises a step of automatically calibrating the beam deflection device and exit beam deflection devices for partially compensating the deflection in the transmitted and diffracted beams. Calibration can be achieved by measuring a deflection angle of the incident beam and direction of the transmitted beam produced by either device in response to a given input signal. The input signal can be for example an electric current flowing through the deflection coils of the beam deflection device and exit beam deflection device. As mentioned above, the deflection of the incident beam and partial deflection compensation of the transmitted and diffracted beam can be controlled by controlling the electric current flowing through deflection coils comprised in the beam deflection device and the exit beam deflection device, respectively. In the calibration step, the sensitivity of the deflection devices such as the deflection coils is determined. For example, an input current flowing through the deflection coils for deflecting the incident beam about a certain angle from the sample or optical axis is determined. Equally, the electric current flowing through the deflection coils of the exit beam deflection device necessary for partially compensating the deflection in the transmitted diffracted and undiffracted beams is determined for a desired degree of compensation. The calibration can be done without a sample. The calibration of the beam deflection device and the exit beam deflection device can, for example be software controlled and performed automatically, before starting an experiment. When the inventive method is performed with a transmission electron microscope, the sensitivity of the deflection elements and the camera length should be calibrated before measuring. This can be automatically controlled by software routine for operating the different components of the transmission electron microscope for performing the calibration steps.

The inventive method preferably further comprises the step of analyzing the detected intensity data depending on the angle of incidence of the incident electron beam. Preferably, the detected intensity data is analyzed in dependency of the angle of incidence of the incident electron beam and the scattering angle of the diffracted beams. The step of analyzing comprises, for example, storing and displaying the detected intensity data, subtracting the background signal, and normalizing. Further, the analysis of the measured intensity data can include fitting the measured intensity of diffraction reflections and reconstruction of structure factor phase information as described by the inventor in "Many-Beam Solution to the phase problem in Crystallography" (arXiv: 0810.3811v1 [cond-mat.mtrl-sci], http://arxiv.org/abs/0810.3811v1) which is incorporated herein by reference.

According to an above described, preferred variant of the inventive method, the angle of incidence is varied, and preferably scanned over a range around the sample axis. In this variant, the intensity of the transmitted diffracted and undiffracted electron beams can be individually detected and saved as separate data files for each angle of incidence. When scanning or varying the angle of incidence in this case, a set of data files for individual angles of incidence is generated with this method. In a preferred embodiment, from a set of data files comprising intensity data of the diffracted or undiffracted transmitted electron beams for various angles of incidence, a data file can be automatically extracted comprising the measured intensity data as a function of the angle of incidence for individual reflections of the transmitted electron beams. This extraction of data can be automatically performed by software.

The inventive method as described above in its various embodiments is preferably performed with a transmission electron microscope (TEM). Conventional transmission electron microscopes can, for example, comprise components such as deflection elements for deflecting an incident beam, a sample stage, deflection elements for deflecting a beam transmitted through the sample, and a detector device for detecting the diffracted beams. Such conventional transmission electron microscope can be operated to perform the inventive method in its various embodiments as described above. A method for operating a transmission electron microscope for automatically performing the steps of the inventive method is an independent aspect of the invention. Operating a transmission electron microscope for performing the inventive method of measuring electron diffraction data, can for example be achieved by software for controlling the components of the transmission electron microscope accordingly.

The control of deflection angle of the incident beam and partial compensation of transmitted beams can also be achieved by a hardware module. A further independent aspect of the invention is a device, configured for deflecting electron beams in an transmission electron diffraction setup, comprising a beam deflection device, configured for deflecting an electron beam illuminating a sample such that the beam hits the sample at an angle of incidence with respect to a sample axis, and an exit beam deflection compensation device, configured for subjecting diffracted and undiffracted beams transmitted through the sample to partial deflection compensation. The beam deflection device and the exit beam deflection compensation device preferably comprise electron optics components such as, for example, deflection coils which can be arranged in an electron diffraction setup such as in a transmission electron microscope for deflecting the beam incident on a sample and partially compensating the deflection in the transmitted diffracted and undiffracted beams. Preferably, the device is configured for measuring electron diffraction of a sample according to the inventive method as described above.

A further independent aspect of the invention is a device configured for deflecting electron beams of a transmission electron microscope, comprising a beam deflection device, configured for operating a transmission electron microscope such that an electron beam illuminating a sample is deflected to hit the sample at an angle of incidence with respect to a sample axis, and an exit beam deflection compensation device, configured for operating a transmission electron microscope such that an electron beam transmitted through the sample is subjected to partial deflection compensation. The beam deflection device and the exit beam deflection compensation device can for example form a hardware component which can be installed on a transmission electron microscope for controlling driving units of electron optics components of the transmission electron microscope. Preferably, the device is configured for measuring electron diffraction of a sample by operating a transmission electron microscope according to the inventive method as described above. A transmission electron microscope comprising such an operating device is an independent aspect of the invention.

The control of the deflection angle and partial deflection compensation by a hardware module can be advantageous, because it can be acting faster than software control. Calibration of the beam deflection device and the exit beam deflection device in this case could be achieved, e.g., manually. Software control of a transmission electron microscope for carrying out the inventive method leads to the advantage, that no manipulation of the hardware of the transmission electron microscope is necessary for performing the inventive method. In view of the costs for a TEM this might be interesting. Further, software control can also automatically perform a calibration routine prior to measurement. Software control further allows for performing versatile experiments, as mentioned in "C. T. Koch, P. Bellina, and P. A. van Aken: "Software Precession Electron Diffraction" in M. Luysberg, K. Tillmannn, T. Weirich (Eds.): EMC 2008, Vol. I: Instrumentation and Methods, pp. 201-202, DOI: 10.1007/978-3-540-85156-1_101, Springer-Verlag Berlin Heidelberg 2008", which is incorporated herein by reference.

Within this application, a beam deflecting device can either comprise electron optics components for varying the direction of an electron beam or a sample stage with a drive for varying a tilt angle of the sample.

A conventional transmission electron microscope comprising electron optics components suitable for deflecting an incident beam illuminating a sample from the optical axis and an exit beam deflection device for deflecting beams transmitted through a sample can also be controlled by software for performing the inventive method for measuring electron diffraction of a sample as described above in its various embodiments. For example, the software can be written as a script within Gatan DigitalMicrograph (www.gatan.com/imaging/dig_micrograph.php) the most widely used image acquisition software installed on transmission electron microscopes. Such a computer program with a program code for controlling a transmission electron microscope to carry out the inventive method as described above in its various embodiments is an independent aspect of the invention. In a preferred embodiment, the software also controls the transmission electron microscope for performing a calibration step for calibrating the electron optics components of the transmission electron microscope, as described above.

A computer program product or digital storage medium with electronically readable data comprising program code for controlling a transmission electron microscope to carry out the inventive method in its various embodiments described above with or without calibration step is a further aspect of the invention. The computer program product can, for example, be distributed residing on a computer readable storage medium or via download from the internet. The computer program can therefore be residing on a computer readable storage medium in form of electronically readable data. The computer-readable storage medium or digital storage medium can be, for example, a hard disk, compact disc, DVD, chip storage medium, flash memory, or other storage device.

The program code in the form of electronically readable data preferably is able to interact with a calculation unit such as, for example, a personal computer or a calculation unit integrated in a transmission electron microscope for controlling a transmission electron microscope.

In a preferred mode for carrying out the invention, a transmission electron microscope is controlled by software to carry out the invention. In this preferred mode, the sample axis is collinear with the optical axis of the TEM and deflection of the incident beam and partial deflection compensation is achieved with electron optics components of the TEM. Preferably, the angle of incidence is scanned over a two-dimensional range around the sample axis, and the transmitted diffracted and undiffracted beams are detected with a two-dimensional detector.

Figure 1:
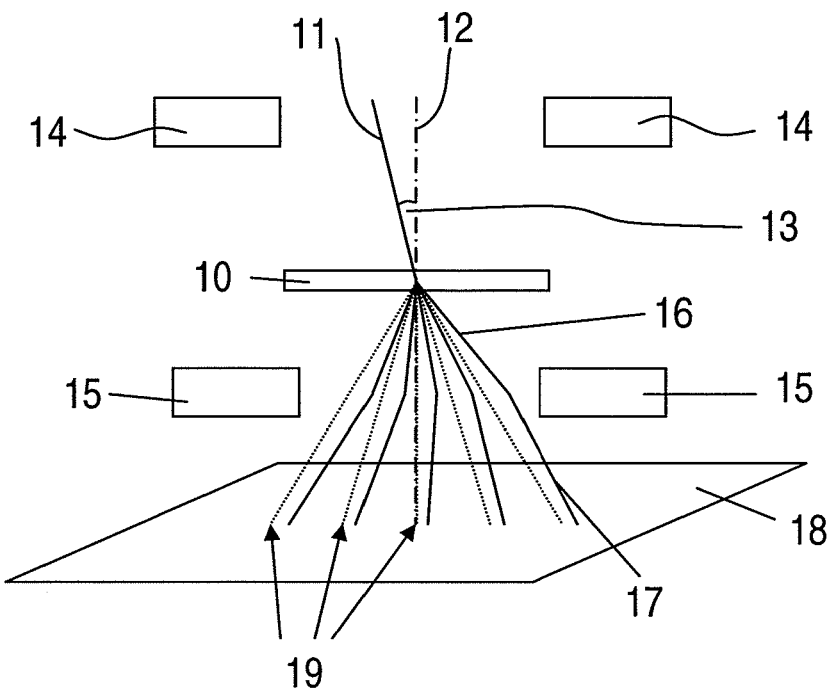
Figure 2:
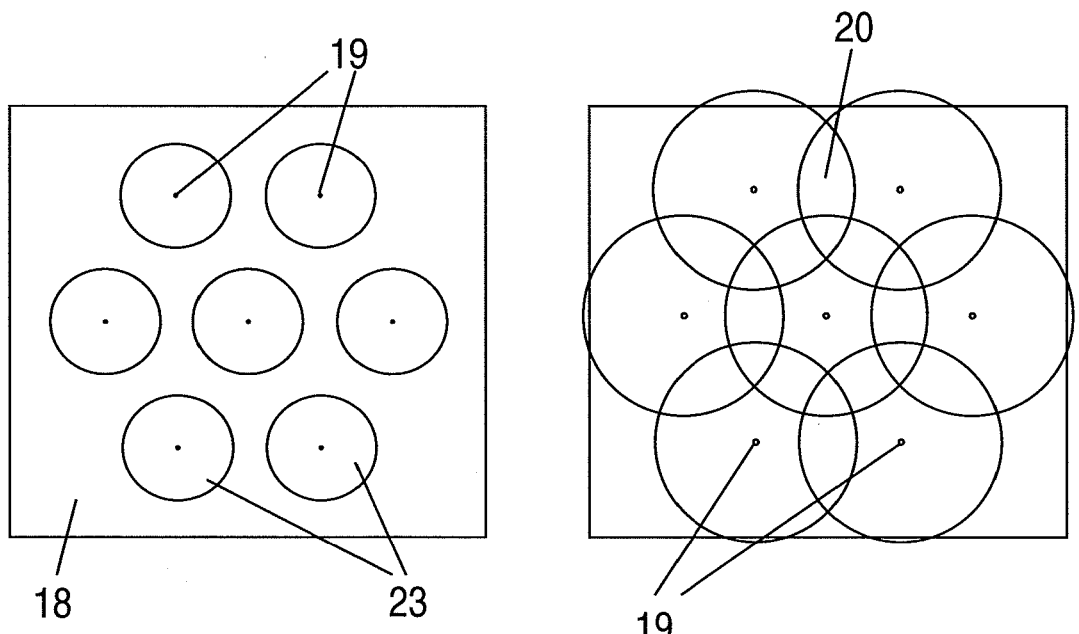
FIG. 2A: an exemplary diffraction pattern of a crystal lattice structure with disc-shaped diffraction reflections.
FIG. 2B: a diffraction pattern of a crystal lattice structure with overlapping disc-shaped diffraction reflections.

According to the inventive method as illustrated in FIG. 1, an electron beam 11 illuminates a sample 10 at an angle of incidence 13 with respect to the sample axis 12. The angle of incidence 13 has been controlled by a beam deflection device comprising deflection coils 14. The beam transmitted through the sample comprises diffracted and undiffracted beams 16 which are subjected to a partial deflection compensation by the exit beam deflection compensation device comprising deflection coils 15. The partially deflection compensated diffracted and undiffracted beams 17 hit a 2-D detector 18. The intensities of the diffracted and undiffracted partially compensated beams are measured as a function of the angle of incidence 13 and the scattering angle which is defined by the position on the 2-D detector. The actual reflection positions 19 are produced by an undeflected beam shown by dotted lines. In case of an undeflected incident beam with an angle of incidence 13 being zero, i.e. with the incident beam collinear with the sample axis 12, would result in deflection reflections at the actual reflection positions 19. By scanning the angle of incidence 13 around the sample axis 12 over an annular range, the diffraction pattern detected on a 2-D detector would for example result in annular patterns 23 around the positions of the reflections 19 as shown in the schematic image of a 2-D detector shown in FIG. 2A. If the angle of incidence is scanned over a two-dimensional range around the sample axis 12, the diffraction patterns of each reflection shown on the detector image would form discs. If the angle of incidence, and in particular the inclination angle becomes large, disc-shaped diffraction patterns of separate reflections in the diffraction pattern would overlap as shown in FIG. 2B. This image shows a diffraction pattern without deflection compensation of the transmitted diffracted and undiffracted beams. According to the inventive method, the deflection is partially compensated after diffraction at the sample, so that the diameter of the disc-shaped diffraction patterns is reduced. Thus, separate diffraction reflections 23 can be detected separately, as shown in FIG. 2A.

FIG. 3 illustrates the angle of incidence of the incident electron beam 11 with respect to the sample axis 12. The sample axis is orientationally fixed to the sample. Preferably, the sample axis is aligned with the optical axis of a transmission electron microscope. The angle of incidence 13 comprises two components, the azimuth angle $\phi$ 22 and the inclination angle $\theta$ 21. When scanning the angle of incidence over an annular range around the sample axis 12, the inclination angle $\theta$ remains constant while the azimuth angle $\phi$ is scanned around the sample axis 12. When the angle of incidence is scanned over a two-dimensional range around the sample axis 12, both components of the angle of incidence, the azimuth angle $\phi$ 22 and the inclination angle $\theta$ 21 are varied.

All aspects and measures of the invention as described within this application can be of significance for the invention both, individually and in combination.

What is claimed is:

1. A method for measuring electron diffraction of a sample, comprising the steps of:
   illuminating the sample with an incident electron beam which is deflected from a sample axis to hit the sample at an angle of incidence relative to the sample axis;
   at least partially subjecting the incident electron beam to diffraction by the sample;
   subjecting diffracted and undiffracted electron beams transmitted through the sample to a partial deflection compensation; and
   detecting an intensity of the diffracted and undiffracted electron beams transmitted through the sample in dependency on the angle of incidence and a scattering angle of the diffracted beam.

2. The method according to claim 1, wherein the sample axis is collinear with an optical axis, and deflection of the incident electron beam from the sample axis is achieved with a beam deflection device comprising electron optics components.

3. The method according to claim 1, wherein the incident electron beam is aligned with an optical axis, and deflection of the incident electron beam from the sample axis is achieved by changing an orientation of the sample relative to the optical axis.

4. The method according to claim 1, further comprising the step of varying the angle of incidence under which the electron beam hits the sample by deflecting the electron beam with a beam deflection device.

5. The method according to claim 1 wherein the intensity of the transmitted and diffracted electron beams is detected two-dimensionally.

6. The method according to claim 1 wherein the partial deflection compensation is achieved by way of an exit beam deflection device prior to detection.

7. The method according to claim 6, wherein the exit beam deflection device comprises electron optics components.

8. The method according to claim 1, wherein the incident electron beam is a substantially parallel beam.

9. The method according to claim 1, wherein the electron beam has an energy in the range of 20 keV to 3000 keV and a bandwith of less than ±1 eV.

10. The method according to claim 4, wherein varying the angle of incidence comprises scanning the angle of incidence over an annular range around the sample axis with all scanned angles of incidence having an identical inclination angle but differing azimuth angle with respect to the sample axis.

11. The method according to claim 4, wherein varying the angle of incidence comprises scanning the angle of incidence over a two-dimensional range around the sample axis with a maximum inclination angle with respect to the sample axis, wherein the two-dimensional range is a member selected from the group consisting of a circular range, an elliptical range, and a square range.

12. The method according to claim 6, further comprising a step of automatically calibrating the beam deflection device and exit beam deflection device for partially compensating the deflection in the transmitted diffracted and undiffracted beams by measuring a deflection angle and direction of the transmitted beam produced by either device in response to a given input signal.

13. The method according to claim 1, further comprising the step of analyzing detected intensity data depending on the angle of incidence of the incident electron beam.

14. The method according to claim 1, wherein a degree of partial deflection compensation is chosen in a range depending on a maximum angle of incidence of the incident beam with respect to the sample axis.

15. The method according to claim 1 wherein the intensity of the transmitted diffracted and undiffracted electron beams is individually detected and saved as a separate data file for each angle of incidence.

16. The method according to claim 15, wherein from a set of data files comprising intensity data of the diffracted or undiffracted transmitted electron beams for various angles of incidence, a data file is extracted comprising measured intensity data as a function of the angle of incidence for individual reflections of the transmitted electron beam.

17. The method according to claim 1, wherein the sample comprises a material sensitive to electron diffraction and is selected from the group consisting of a two-dimensional crystal, a three-dimensional crystal, a protein crystal, a quasicrystal, and a polycrystalline material.

18. A method for operating a transmission electron microscope, comprising automatically performing the steps of the method of claim 1.

19. A device for measuring electron diffraction of a sample according to the method of claim 1, said device comprising:
   a beam deflection device, configured for deflecting an electron beam illuminating a sample such that the beam hits the sample at an angle of incidence with respect to a sample axis, and
   an exit beam deflection compensation device, configured for subjecting a beam transmitted through the sample to partial deflection compensation.

20. A device for measuring electron diffraction of a sample according to the method of claim 1, said device comprising:
   a beam deflection device, configured for operating a transmission electron microscope such that an electron beam illuminating a sample is deflected to hit the sample at an angle of incidence with respect to a sample axis, and
   an exit beam deflection compensation device, configured for operating a transmission electron microscope such that an electron beam transmitted through the sample is subjected to partial deflection compensation.

21. A transmission electron microscope comprising a device according to claim 20.

22. Computer program product residing on a computer-readable storage medium comprising a program code for controlling a transmission electron microscope to carry out the method according to claim 1.

23. Computer program product residing on a computer-readable storage medium comprising a program code for controlling a transmission electron microscope to carry out the method according to claim 12.

24. Digital storage media with electronically readable data comprising program code for controlling a transmission electron microscope to carry out the method according to claim 1.

25. Digital storage media with electronically readable data comprising program code for controlling a transmission electron microscope to carry out the method according to claim 12.

* * * * *